(12) United States Patent
de Paula et al.

(10) Patent No.: US 9,248,235 B2
(45) Date of Patent: Feb. 2, 2016

(54) CORE APPARATUS CONNECTABLE TO A VARIETY OF SENSORS, FLUID DELIVERY DEVICES AND OTHER DEVICES TO FORM A SYSTEM, SUCH AS FOR DIABETES MANAGEMENT SYSTEM

(76) Inventors: Guilherme Jose Enne de Paula, San Francisco, CA (US); Jerry K. Joseph, Knoxville, TN (US)

( * ) Notice: Subject to any disclaimer, the term of this patent is extended or adjusted under 35 U.S.C. 154(b) by 822 days.

(21) Appl. No.: 13/434,811

(22) Filed: Mar. 29, 2012

(65) Prior Publication Data

US 2012/0302990 A1 Nov. 29, 2012

Related U.S. Application Data

(60) Provisional application No. 61/468,670, filed on Mar. 29, 2011.

(51) Int. Cl.
*A61M 5/172* (2006.01)
*A61M 5/142* (2006.01)
*A61M 5/168* (2006.01)

(52) U.S. Cl.
CPC .......... *A61M 5/1723* (2013.01); *A61M 5/14248* (2013.01); *A61M 5/16827* (2013.01); *A61M 2205/3584* (2013.01); *A61M 2205/50* (2013.01); *A61M 2205/82* (2013.01); *A61M 2230/06* (2013.01); *A61M 2230/201* (2013.01); *A61M 2230/30* (2013.01); *A61M 2230/50* (2013.01)

(58) Field of Classification Search
CPC .......... A61M 5/1723; A61M 5/14248; A61M 2230/06; A61M 5/16827; A61M 2230/30; A61M 2230/201; A61M 2205/3584; A61M 2205/82; A61M 2205/50; A61M 2230/50
USPC .......................... 604/65–67, 891.1, 504, 115
See application file for complete search history.

(56) References Cited

U.S. PATENT DOCUMENTS

| | | | | |
|---|---|---|---|---|
| 5,997,501 | A * | 12/1999 | Gross et al. | 604/65 |
| 6,071,258 | A * | 6/2000 | Dalke et al. | 604/5.01 |
| 8,133,197 | B2 * | 3/2012 | Blomquist et al. | 604/66 |
| 2002/0169439 | A1* | 11/2002 | Flaherty | 604/891.1 |
| 2009/0062767 | A1* | 3/2009 | Van Antwerp et al. | 604/504 |

* cited by examiner

*Primary Examiner* — Manuel Mendez
(74) *Attorney, Agent, or Firm* — Jerry K. Joseph

(57) ABSTRACT

A core apparatus connectable to at least one sensor and to at least one fluid delivery device which includes a base housing, a connection hub to couple to the at least one sensor and to the at least one fluid delivery device, and a controller disposed within the base housing to communicate with the at least one sensor and to the at least one fluid delivery device, wherein the controller forms a continuous feedback loop with the at least one sensor and the at least one fluid delivery device.

21 Claims, 15 Drawing Sheets

CORE APPARATUS CONNECTABLE TO A VARIETY OF SENSORS, FLUID DELIVERY DEVICES AND OTHER DEVICES TO FORM A SYSTEM, SUCH AS FOR DIABETES MANAGEMENT SYSTEM

CROSS-REFERENCE TO RELATED APPLICATIONS

This application claims the benefit of U.S. Provisional Patent Application No. 61/468,670, filed on Mar. 29, 2011, the disclosure of which is incorporated herein in its entirety by reference.

BACKGROUND OF THE INVENTION

1. Field of the Invention

The present general inventive concept relates generally to devices for delivering therapeutic fluids, and more particularly to a non-disposable core device adaptable to communicate with a plurality of sensor devices and/or a plurality of disposable drug or fluid delivery devices. Furthermore, the present general inventive concept relates to an upgradeable core device configured to be able to connect and communicate to a sensor device, a fluid (e.g., a drug) delivery device, and any combinations thereof.

2. Background of the Invention

There currently exists several diseases and conditions which are monitored and/or treated by medicines. These diseases may be diagnosed and treated based upon the existence or non-existence of particular enzymes, proteins, glucose, and other chemicals within a patient's body.

For instance, one particular disease is diabetes which can be characterized by the absence or improper utilization of insulin secreted by a patient's pancreas. Insulin is used by the body to facilitate the delivery of glucose into cells. Typically, in mammals, the body maintains a blood glucose level at a range between 64.8 and 104.4 mg/dL. Glucose is the main source of energy for body cells and is transported throughout the body through the bloodstream. Glucose requires the hormone insulin in order to be absorbed by the body cells.

SUMMARY OF THE INVENTION

The present general inventive concept relates to a universal core connection device configured to connect to a plurality of sensors and a plurality of drug delivery devices and which communicates to an external device. The universal core connection device may wirelessly communicate to the external device (i.e., mobile device).

The present general inventive concept further relates to an upgradeable core device configured to be able to connect and communicate to a sensor device, a fluid (e.g., a drug) delivery device, and an external mobile device.

The present general inventive concept provides for a core apparatus connectable to at least one sensor and to at least one fluid delivery device, the core apparatus including a base housing, a connection hub to couple to the at least one sensor and to the at least one fluid delivery device, and a controller disposed within the base housing to communicate with the at least one sensor and to the at least one fluid delivery device, wherein the controller forms a continuous feedback loop with the at least one sensor and the at least one fluid delivery device.

The controller may control operations of the at least one sensor and the at least one fluid delivery device.

The at least one sensor may be connectable to a user to measure the user's body signals. The body signals may include the user's blood glucose level, vital readings, cholesterol, analytes, hormone, blood pressure, and Oxygen level. The at least one sensor and at least one fluid delivery device may be formed to surround the base housing.

The base housing may be formed in a triangular shape, a rectangular shape, a circular shape, a pentagon shape, or a combination thereof.

The fluid delivery device may deliver a fluid stored therein to a user. The fluid includes at least one of insulin and glucagon.

The controller may control operations of each of the at least one sensor and the at least one fluid delivery device attached to the connection hub.

The core apparatus may further include a power source disposed within the base housing to provide voltage to the controller, to the at least one sensor, and to the at least one fluid delivery device.

The controller may wirelessly communicate to an external device to control an operation of the at least one sensor and the at least one fluid delivery device.

The present general inventive concept also provides a health treatment system including a core apparatus in communication with an external device, the external device having a plurality of configurations, a sensor device having a sensor to detect a body signal from a user connectable to the core apparatus, and a first fluid delivery device having a first fluid storage compartment to store a first fluid and a first fluid dispensing mechanism to deliver the first fluid to the user connectable to the core apparatus, wherein the core apparatus instructs the external device to operate in a first configuration when only the at least one sensor device is coupled to the core apparatus, a second configuration when only the first fluid delivery device is coupled to the core apparatus, and a third configuration when both the at least one sensor device and the first fluid delivery device are coupled to the core apparatus.

The health treatment system may further include a second fluid delivery device having a second fluid storage compartment to store a second fluid and a second fluid dispensing mechanism to deliver the second fluid to the user.

The core apparatus may instruct the external device to operate in a fourth configuration when the at least one sensor device, the first fluid delivery device, and the second fluid delivery device are coupled to the core apparatus. The external device may be a mobile device.

The core apparatus may communicate to the external device through at least one of Bluetooth™, Bluetooth Low Energy™, WiFi, Zigbee™, ANT™, and ANT+™.

The sensor of the at least one sensor device may include a glucose sensor, a cholesterol sensor, a blood pressure sensor, an oxygen sensor, an analyte sensor, a heart rate sensor, and a body temperature sensor.

The core apparatus may transmit and receive data to/from the external device to allow for a continuous feedback loop between the at least one sensor device, the first fluid delivery device, the second fluid delivery device, and the external device.

The at least one sensor may be attached to a user to measure the user's glucose level and to transmit a sensor data corresponding to the measured glucose level to the core apparatus, the core apparatus to control the first fluid delivery device and the second fluid delivery device to deliver the first and second fluid according to the user's predetermined limits.

The user's predetermined target may stored within the external device. The target refers to a specific target of sensed data. For instance, if the user's predetermined target was defined at 110 mg/dL (for glucose), the external device and/or the core apparatus may control functions of the wedges to deliver fluids and or medication so that the user is maintained at 110 mg/dL.

The present general inventive concept also provides for a method of using a disease management system which includes removably attaching a sensor device to a core apparatus, the core apparatus having a sensor to measure a body signal of a user and a controller to control an operation of the core apparatus, removably attaching a first fluid delivery system to the core apparatus, the first fluid delivery system having a first fluid compartment and a first fluid delivery device to store and deliver a first fluid, and removably attaching a second fluid delivery system to the core apparatus, the second fluid delivery system having a second fluid compartment and a second fluid delivery device to store and deliver a second fluid, wherein the core controller receives the body signal from the sensor device and controls the delivery of the first fluid and the second fluid based on the body signal.

Additional aspects of the present general inventive concept will be set forth in part in the description which follows and, in part, will be obvious from the description, or may be learned by practice of the general inventive concept.

BRIEF DESCRIPTIONS OF THE DRAWINGS

These and/or other aspects of the present general inventive concept will become apparent and more readily appreciated from the following description of the embodiments, taken in conjunction with the accompanying drawings of which:

DETAILED DESCRIPTION

Figure 1:
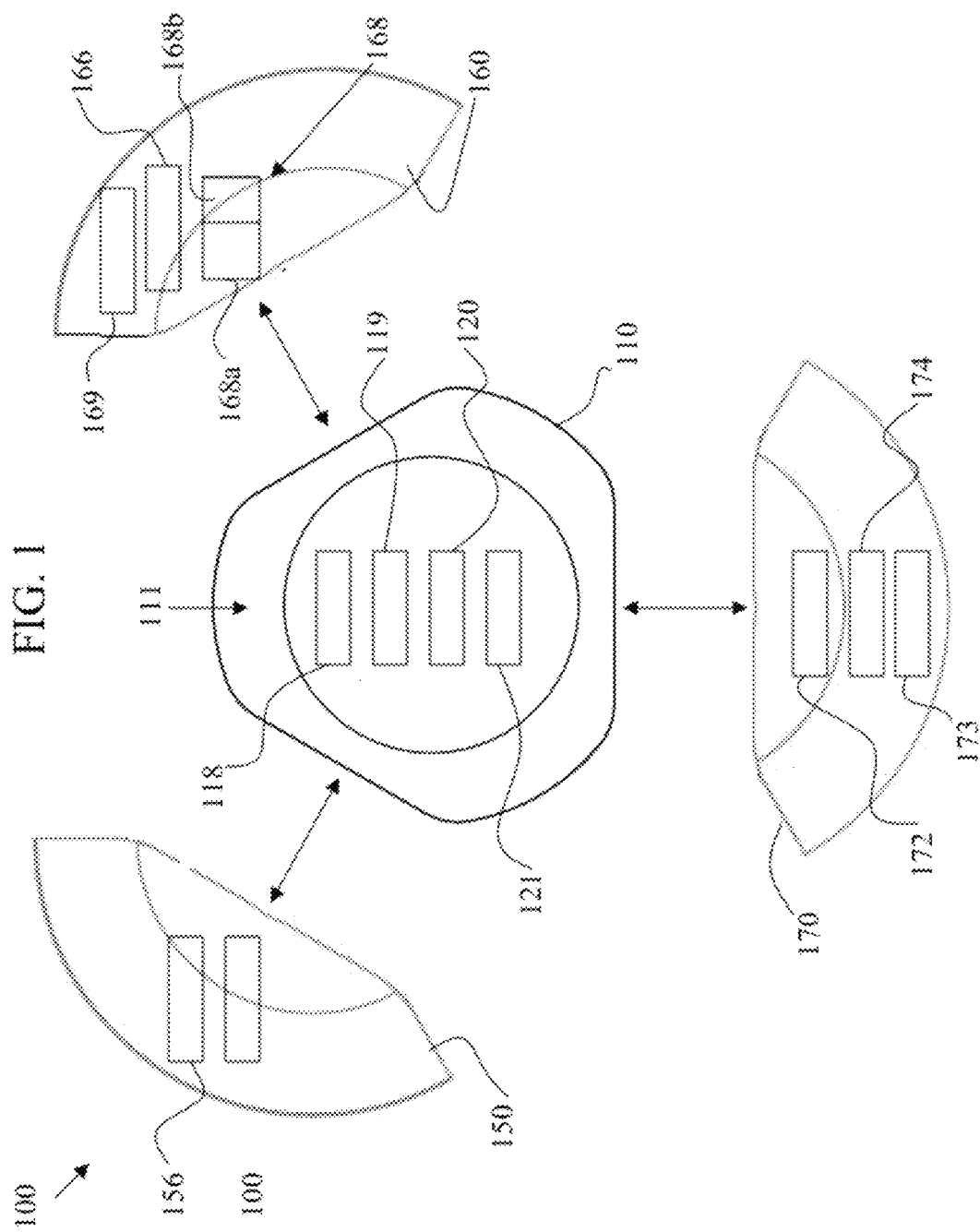
FIG. 1 is an exploded schematic top view of the artificial pancreatic system according to the present general inventive concept.

Reference will now be made in detail to the exemplary embodiments of the present general inventive concept, examples of which are illustrated in the accompanying drawings, wherein like reference numerals refer to the like elements throughout. The exemplary embodiments are described below in order to explain the present general inventive concept by referring to the figures.

FIG. 1 illustrates an exploded schematic top view of the artificial pancreatic system according to the present general inventive concept. The artificial pancreatic system, generally designated as reference numeral 100, includes a core apparatus 110, a disposable sensor device 150, a first disposable fluid delivery device 160, and a second disposable fluid delivery device 170, referred to as "wedges". However, the present general inventive concept is not limited thereto. That is, in exemplary embodiments, the artificial pancreatic system 100 may consist of the core apparatus 110 coupled to a various single disposable sensor device(s) 150 (e.g. sensor wedge) and/or various disposable fluid delivery device(s) 160, 170 (e.g., fluid delivery wedges).

In the current exemplary embodiment, the core apparatus 110 acts as a connection hub to which the plurality of sensor devices 150 and/or plurality of disposable fluid delivery devices 160, 170 may be electrically and/or mechanically coupled. The core apparatus 110 may include a common interconnecting device or bus 118 which allows the core apparatus 110 to communicate with the sensor device 150 and to each of fluid delivery devices 160, 170 attached to the core apparatus 110. The core apparatus 110 may provide for a continuous communication feedback loop between the variety of sensor devices 150 and the variety of fluid delivery devices 170 coupled to the core apparatus 110.

The core apparatus 110 may include one or more CPUs 119 or micro-controllers used to control operations of each of the sensor devices 150 and each of the fluid delivery devices 170 that are attached to the core apparatus 110. The core apparatus 110 may communicate to a hand-held device 200 and to each of the sensor devices 150 and the fluid delivery devices 160, 170 wirelessly or via a wired connection. The wireless communication may be achieved through Bluetooth, Bluetooth Low Energy, WiFi, Zigbee, ANT, ANT+ or various other wireless communication protocols. In an exemplary embodiment, the core apparatus 110 communicates to the hand-held device 200 via Bluetooth low energy and the core apparatus 110 communicates to each of the sensor and fluid delivery devices connected thereto via an electrical connection. The hand-held device 200 may communicate to the sensor and fluid delivery devices via the core apparatus 110. However, the present general inventive concept is not limited thereto.

That is, in exemplary embodiments, the hand-held device 200 may communicate directly to the sensor and/or the fluid delivery devices.

In exemplary embodiments, the core apparatus 110 may further include a power source 120 to provide voltage to operate each of the sensor devices 150 and each of the fluid delivery devices 160, 170 coupled to the core apparatus 110. In exemplary embodiments, the power source 120 may include lithium and/or various other types of rechargeable (via USB or induction) or disposable power supplies, batteries or fuel cells. In another exemplary embodiment, the power source 120 may convert heat generated by the user into energy, which is then used to operate at least one of the core apparatus 110, the sensor device 150, and the fluid delivery devices 160, 170.

Figure 2:
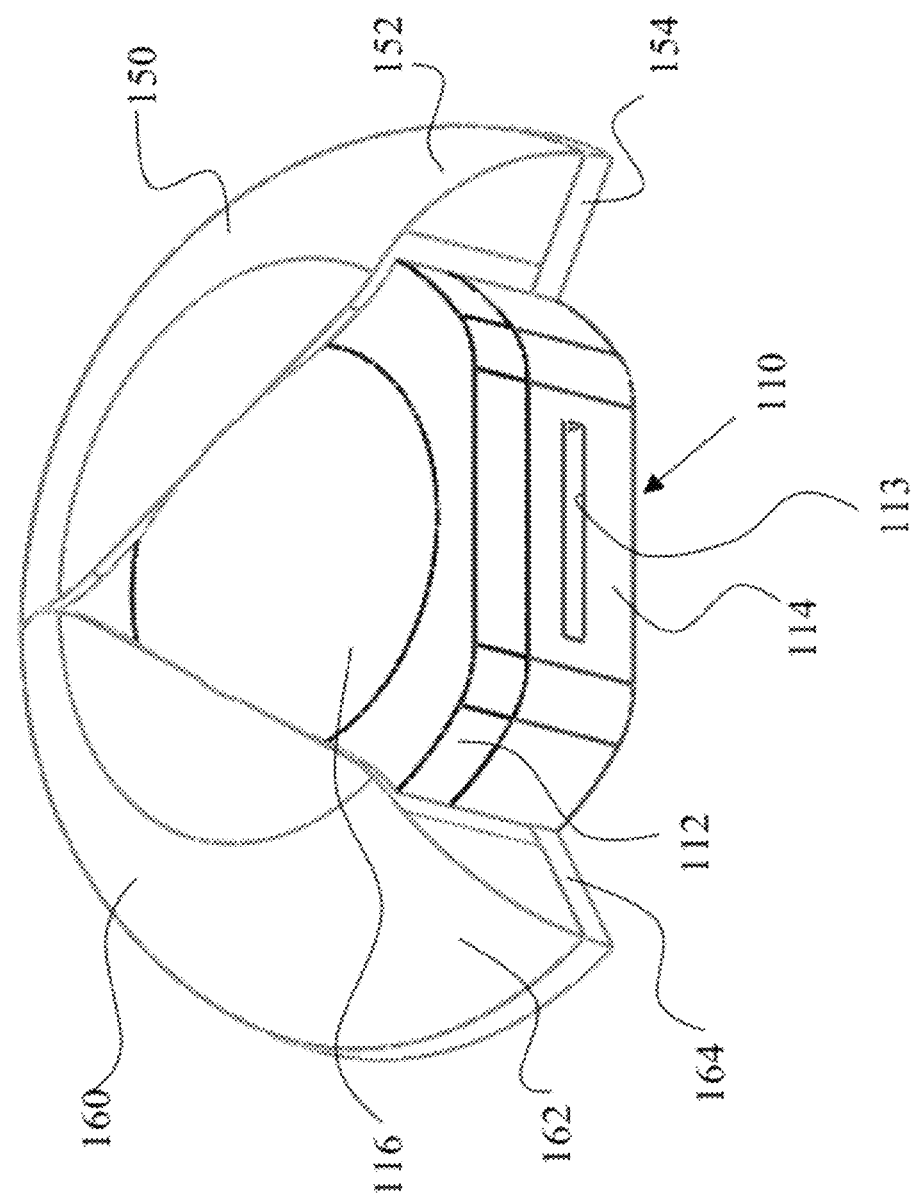
FIG. 2 is a perspective schematic side view of the artificial pancreatic system according to the present general inventive concept.

FIG. 2 is a perspective schematic side view of the artificial pancreatic system according to the present general inventive concept. Referring to FIG. 2, the core apparatus 110 includes a top core housing 112 and a base core housing 114, which form a cavity therebetween to store the core CPU(s) 119. The disposable sensor device 150 includes a wedge base 152 and a wedge cover 154 which form a cavity therebetween to store a wedge CPU 119 and various other wedge components. In exemplary embodiments, a fluid delivery wedge base 162 and a fluid delivery wedge cover 164 may be used for the disposable fluid delivery device 160, and may be substantially similar to the wedge base 152 and the wedge cover 154, respectively.

Referring now to FIGS. 1 and 2, in exemplary embodiments, the core apparatus 110 is connectable to plurality of sensors devices 150 and to a plurality of fluid delivery devices 160, 170. The core apparatus 110 includes a base housing 111 which is formed by the top core housing 112 and the base core housing 114. The core apparatus 110 includes a connection hub 113, which electrically and/or mechanically connects to the plurality of sensors devices 150 and the plurality of fluid delivery devices 160, 170 to the core apparatus 110.

The core apparatus 110 further includes a controller 121 disposed within the base core housing 114 which communicates and/or controls the functions of the plurality of sensors 150 and the plurality of fluid delivery devices 160, 170 such that the controller 121 forms a continuous communication feedback loop between the plurality of sensor devices 150, the plurality of fluid delivery devices 160, 170, the core apparatus 110 and the hand-held device 200.

In exemplary embodiments, the core apparatus 110 may be configured to include a universal driver which allows the core apparatus 110 to communicate with and/or control a variety of sensor devices, delivery devices, and hand held devices manufactured by a variety of different companies, according to varying specifications.

The plurality of sensors 150 is configured to be connectable to a user (i.e., a patient) to measure various body signals from the patient. The body signals may include the user's blood glucose level, vital readings, cholesterol, and various other body measurements. However, the present general inventive concept is not limited thereto. That is, the plurality of sensors 150 may include sensors that may measure body temperature, heart rate, and exercise activity of the user.

In exemplary embodiments, the fluid delivery device 160 includes a fluid storage compartment 166 to store liquids such as medicines, insulin, hormones, glucagon, electrolytes and glucose solutions and the like, and a fluid delivery device (i.e., needle mechanism) 168 to administer the stored fluid to a patient. However, the present general inventive concept is not limited thereto. That is, the fluid delivery device 160 may be configured to deliver a wide variety of fluids including antibiotics, nutritional fluids, analgesics, anticoagulants, or chemotherapeutics. In the present exemplary embodiment, the fluid storage compartment 166 is formed in an arc shape so as to correspond to an exterior contour of the fluid delivery devices 160, 170. In further exemplary embodiments, the cross-section of the fluid storage compartment 166 is elliptically shaped.

The needle mechanism 168 is used to deliver a calculated amount of the liquid stored in the storage compartment 166 into the patient or user. In exemplary embodiments, the core apparatus 110 may be used to manage diseases and conditions such as diabetes, heart disease, cancer, and health conditions such as high or low blood pressure and cholesterol, pain, and pregnancy. The fluid delivery device 168 may further include a hypodermic needle 168A and a flexible cannula 168B disposed on needle 168A to administer the fluid stored in the fluid storage compartment 166 into the user. The hypodermic needle 168A may be forced into the user to a predetermined depth by a force applied to the needle 168A, thereby inserting the cannula 168B into the user at a desired depth "D" (see FIG. 12). In an exemplary embodiment, the elastic and/or static force of the needle 168A created when bent (i.e., bent state, see FIG. 11) may be used to insert the needle 168A and cannula 168B into the user at a depth of 2 to 8 mm, when released in a deployed state (see FIG. 12). More preferably, the needle 168 would retract after inserting the cannula 168B into the user at a depth between 3 and 5 mm. However, the present general inventive concept is not limited thereto. That is, in alternative exemplary embodiments, the needle 168A and the cannula 168B may be inserted into the user by a spring force.

Figure 3:
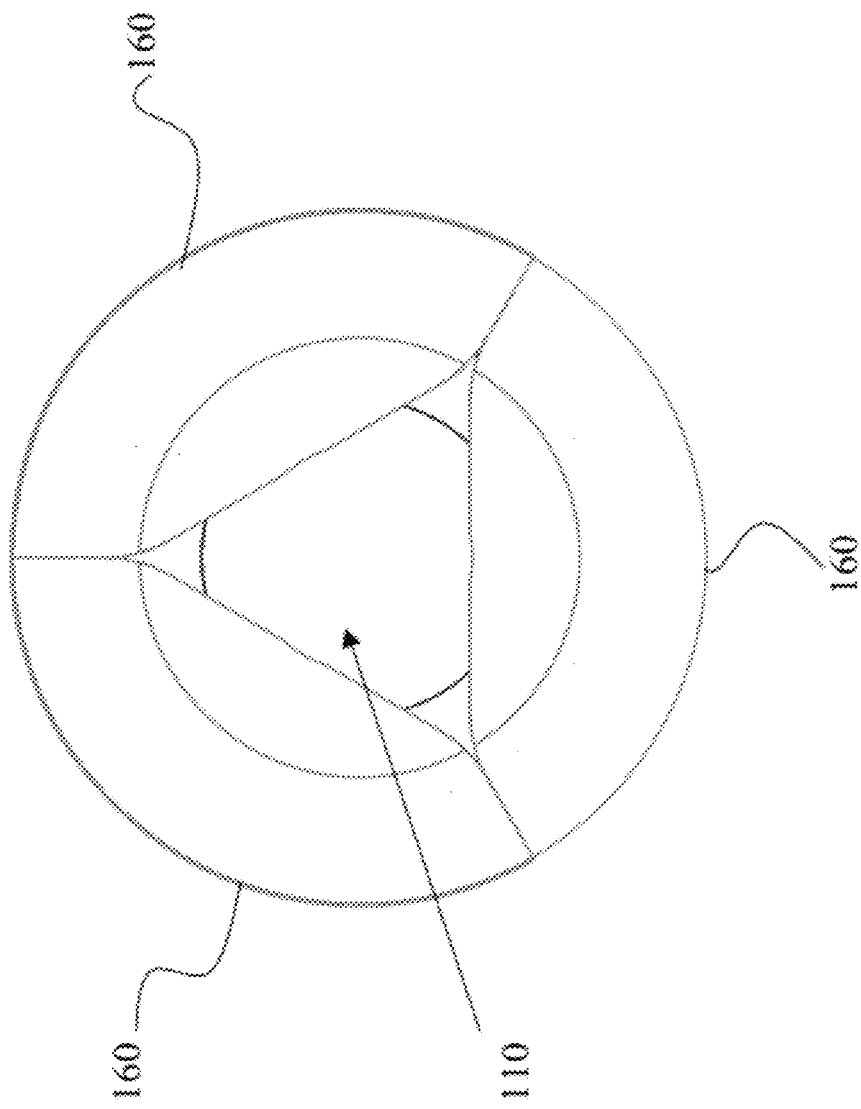
FIG. 3 is a perspective top view of the artificial pancreatic system in an assembled state according to the present general inventive concept.

FIG. 3 is an assembled perspective top view of the artificial pancreatic system according to the present general inventive concept. Referring to FIG. 3, the sensor devices 150 and/or the fluid delivery devices 160, 170 may be formed in a shape so as to surround the core apparatus 110 in various shapes. In the current exemplary embodiment, the core apparatus 110 may be formed in a circular shape and each of the sensors and fluid delivery devices may be formed in a wedge shape (see FIGS. 1 and 3) so as to connect to an outer perimeter of the core apparatus 110. However, the present general inventive concept is not limited thereto. That is, the plurality of sensor devices 150 and the plurality of fluid delivery devices 160, 170 are formed to surround the base housing 111 of the core apparatus 110.

In alternative exemplary embodiments, the core apparatus 110 may be formed in various shapes such as a triangular shape, a square shape, a pentagon shape, combinations thereof or various other shapes and each of the sensor devices 150 and the fluid delivery devices 160, 170 may be formed in such shapes so as to surround the core apparatus 110. In addition, the external shape of the core apparatus 110 may vary depending on a number of devices connected to the core apparatus 110.

In exemplary embodiments, the core apparatus 110 and each of the sensor devices 150 and the fluid delivery devices may be attached to a user's body by using an adhesive pad.

In exemplary embodiments, the core apparatus 110 may be connected to only a single sensor device 150 or a single fluid delivery device (e.g., wedge) to implement a continuous glucose monitor or an insulin delivery system. An application or program running on the hand-held device 200 would request information from the core apparatus 110 and the wedges 150, 160, and 170 and would determine the number and the types of wedges currently connected to the core apparatus 110, based on information stored within a non-volatile device or memory 156 on the wedges. The information would include the wedges unique identification information such as an ID number, parameters and drivers. That is, the non-volatile device or memory 156, 169, 173 within the wedges would store unique identification information of the particular wedge, such as the type of sensor used, the type of fluid stored within the delivery device, the manufacturing serial number, and the like. The core apparatus 110 would read the unique identification information from each wedge connected to the core apparatus 110. The application stored on the hand-held device 200 and the core apparatus 110 would then automatically configure itself as an Insulin Pump, a Continuous Glucose Monitor, a Glucagon Pump, or any combination of the these functionalities according to which sensors and/or which fluid delivery wedges are connected to the core apparatus 110. In addition, if all three types of wedges are connected to the core, the application and the core apparatus 110 would recognize the artificial pancreatic system configuration and would therefore run as an artificial pancreatic system. The external device 200 may automatically configure itself according to a signal received from the core apparatus 110, corresponding to identifications of the types of wedges attached to the core apparatus 110 and/or the types of medications or drugs disposed within the fluid storage compartments of the fluid delivery devices.

In the present exemplary embodiment, the core apparatus 110 is configured to manage all types of diabetes. A first fluid delivery device 160 may store and deliver a first fluid, such as insulin or glucagon. A second fluid delivery device 170 may store and deliver a second fluid, such as insulin or glucagon. In exemplary embodiments, the first fluid may be a slow acting medication (i.e., slow acting insulin) and the second fluid may be a faster acting medication (i.e., fast acting insulin). The core apparatus 110 can calculate an amount of the first and second fluid that is to be delivered to a patient according to predetermined algorithms. In an exemplary embodiment, the core apparatus 110 can calculate the amount of first and second fluid to deliver to a patient according to the measured body signals received from the sensor device 150. However, the present general inventive concept is not limited thereto. That is, in exemplary embodiments, the artificial pancreatic system 100 may be configured to manage various other diseases.

Figure 4:
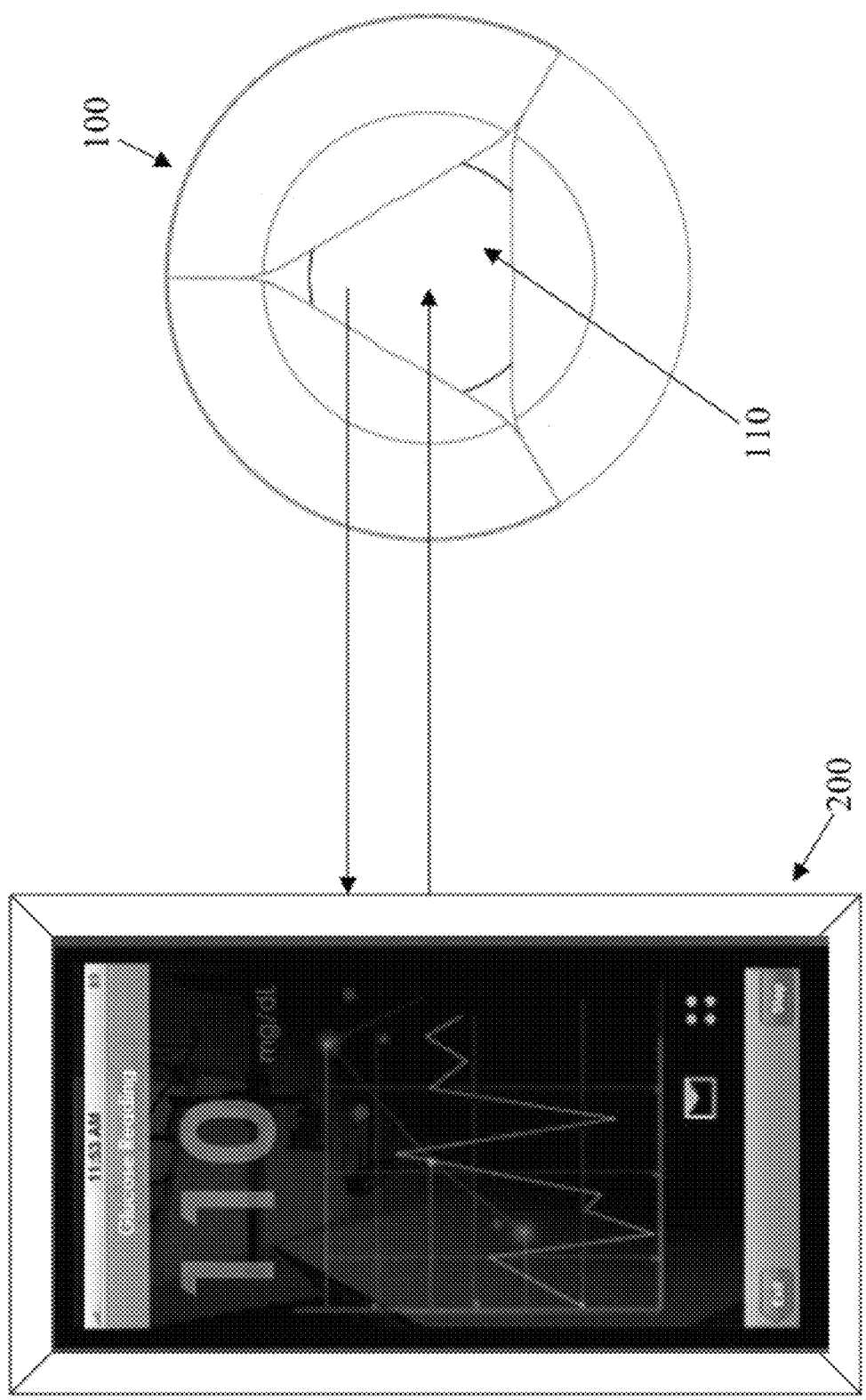
FIG. 4 is a schematic view illustrating a method of using the artificial pancreatic system according to an exemplary embodiment of the present general inventive concept.

In exemplary embodiments, a user may control and monitor operations of the artificial pancreatic system 100 through a hand-held device 200 (see FIG. 4) which communicates with the core apparatus 100 wirelessly or via a wired connection. For instance, the core apparatus 110 is coupled to at least one sensor device 150 (e.g. glucose monitor) and to at least one fluid delivery device 160 (e.g., first fluid delivery device). The glucose sensor device 150 is attached to a patient's body and would continuously monitor a user's blood glucose level and would then transmit a signal to the hand-held device 200 via the core apparatus 110.

In an exemplary embodiment, the glucose sensor will transmit a particular glucose level of the user so that the hand-held device 200 and/or the core apparatus 110 could use this information to determine whether the user's glucose level is within a predetermined range or a specific target. The user may define an acceptable glucose level range or a specific target from the hand-held device 200. In other words, if the user's blood glucose level falls outside of this acceptable range, the hand-held device 200, based on pre-determined parameters would manually or automatically calculate and transmit a warning signal or command to the core apparatus 110. The core apparatus 110 would then issue a delivery signal to the first fluid delivery device (e.g., insulin) and to the second fluid delivery device (e.g., glucagon) to thereby regulate the user's blood glucose level to be within the predetermined acceptable range. In alternative exemplary embodiments, the application stored on the hand-held device 200 could automatically contact a healthcare provider via e-mail, text message, wireless communication, or by initiating a phone call in case any sensor or fluid delivery data is at or above threshold levels, as defined by the user. The hand-held application could also, in wireless or wired form, upload all information about glucose levels, insulin delivery, glucagon delivery, or any other activities such as meals, exercising, BG meter reading and others to a personal computer where it would be available on a server, so that healthcare providers can readily access that information.

The core apparatus 110, the sensor wedge 150, and the fluid delivery wedge 160, 170 would form a continuous feedback loop which would simultaneously monitor and deliver a drug (s), if necessary, to thereby maintain control of a user's blood glucose level, for instance. However, the present invention is not limited thereto. That is, the artificial pancreatic system according to the present invention may also be used to measure a wide variety of body signals from a user, monitor these signals, and deliver a wide variety of drugs, if necessary, to thereby maintain control or treat a particular condition. For instance, the present invention may be suitable for pregnant females who require continuous monitoring of certain body and fetus signals and delivery of a specific drug to control various biological variables. In an alternative embodiment, the present invention may be suitable for people with a cardiac condition that may be monitored by the sensor wedge and medicated by the fluid delivery wedge(s). In addition, it could be used for a patient that has recently been discharged from a healthcare facility and needs to have several vital signs (heart rate, blood pressure, temperature, glucose, cholesterol or others) remotely monitored and/or medication delivered during the critical hospital-to-home transitional period as well as to comply with a home care plan. Furthermore, an embodiment according to the present general inventive concept could be used for an athlete that needs to have several vital signs remotely monitored (heart rate/pulse, blood pressure, temperature, glucose or others) and/or electrolytes, glucose or other substances delivered to the body to improve performance and/or allow the athlete to endure long periods of exercise without having to interrupt the activity.

In exemplary embodiments, the core apparatus 110 would further include a blood glucose monitor wedge 150, a first fluid delivery wedge 160, and a second fluid delivery wedge 170. The first fluid delivery wedge 160 would deliver insulin to the user and the second fluid delivery wedge 170 would deliver glucagon to the user. In addition, the first fluid delivery wedge 160 could be used to deliver amylin or a mixture of insulin and amylin, and the second fluid delivery wedge 170 would deliver glucagon, thereby creating a 3-hormone artificial pancreatic system.

Figure 5:
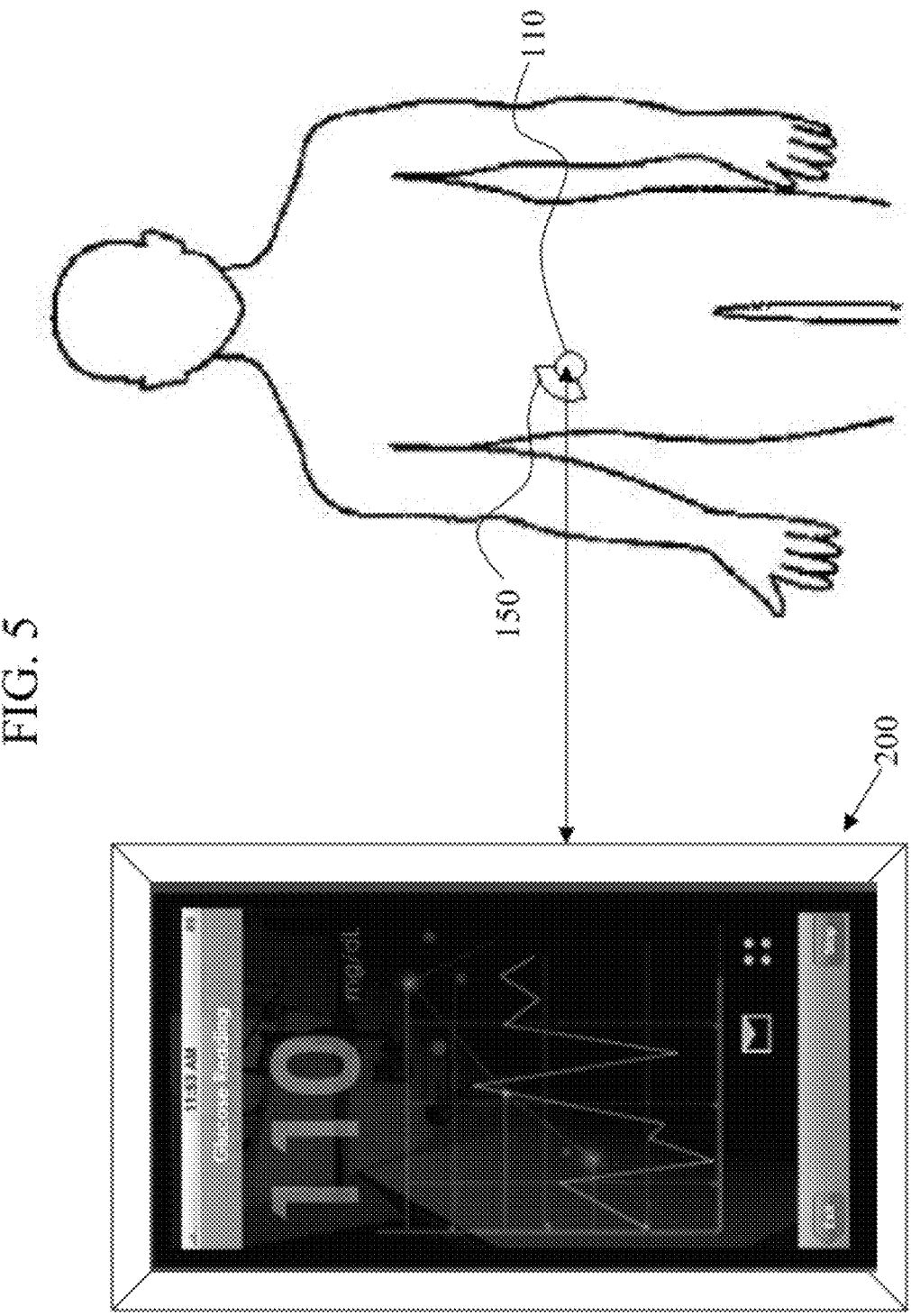
FIG. 5 is a front view of a core apparatus coupled to a sensor device shown attached to a user and a remote hand-held device for use with the core apparatus and the sensor device, according to an exemplary embodiment of the present general inventive concept.

FIG. 5 is a front view of a core apparatus 110 coupled to a sensor device 150 shown attached to a user and a remote hand-held device 200 for use with the core apparatus 110 and the sensor device 150, according to an exemplary embodiment of the present general inventive concept.

Figure 6:
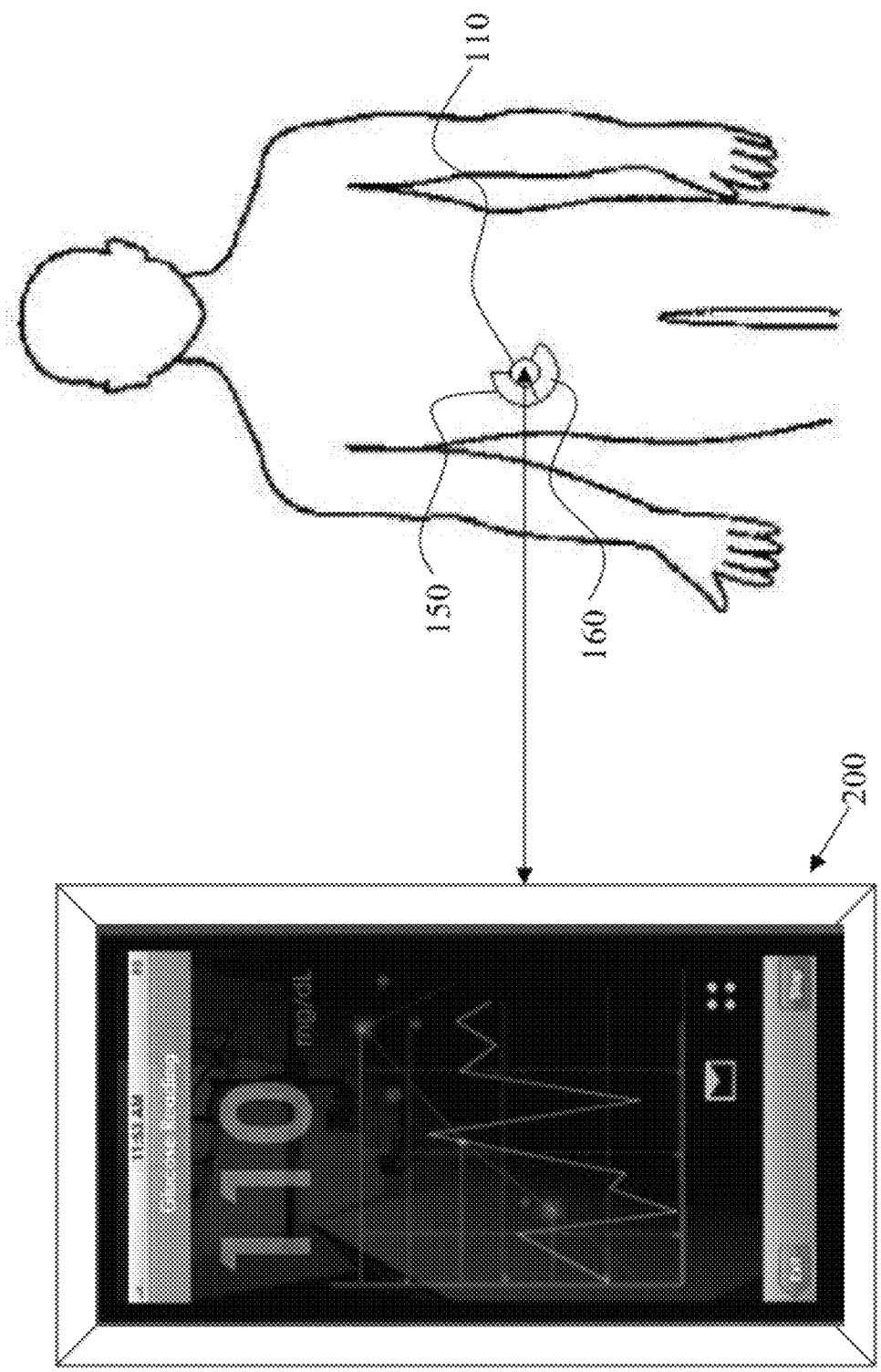
FIG. 6 is a front view of a core apparatus coupled to a sensor device and a fluid delivery device shown attached to a user and a remote hand-held device for use with the core apparatus, the sensor device, and the fluid delivery device, according to an exemplary embodiment of the present general inventive concept.

FIG. 6 is a front view of a core apparatus 110 coupled to a sensor device 150 and a fluid delivery device 160 shown attached to a user and a remote hand-held device 200 for use with the core apparatus 110, the sensor device 150, and the fluid delivery device 160, according to an exemplary embodiment of the present general inventive concept. However, the present general inventive concept is not limited thereto. That is, the core apparatus 110 may only be connected to a fluid delivery device 160 to deliver a fluid according to instructions received from the hand-held device 200.

Figure 7:
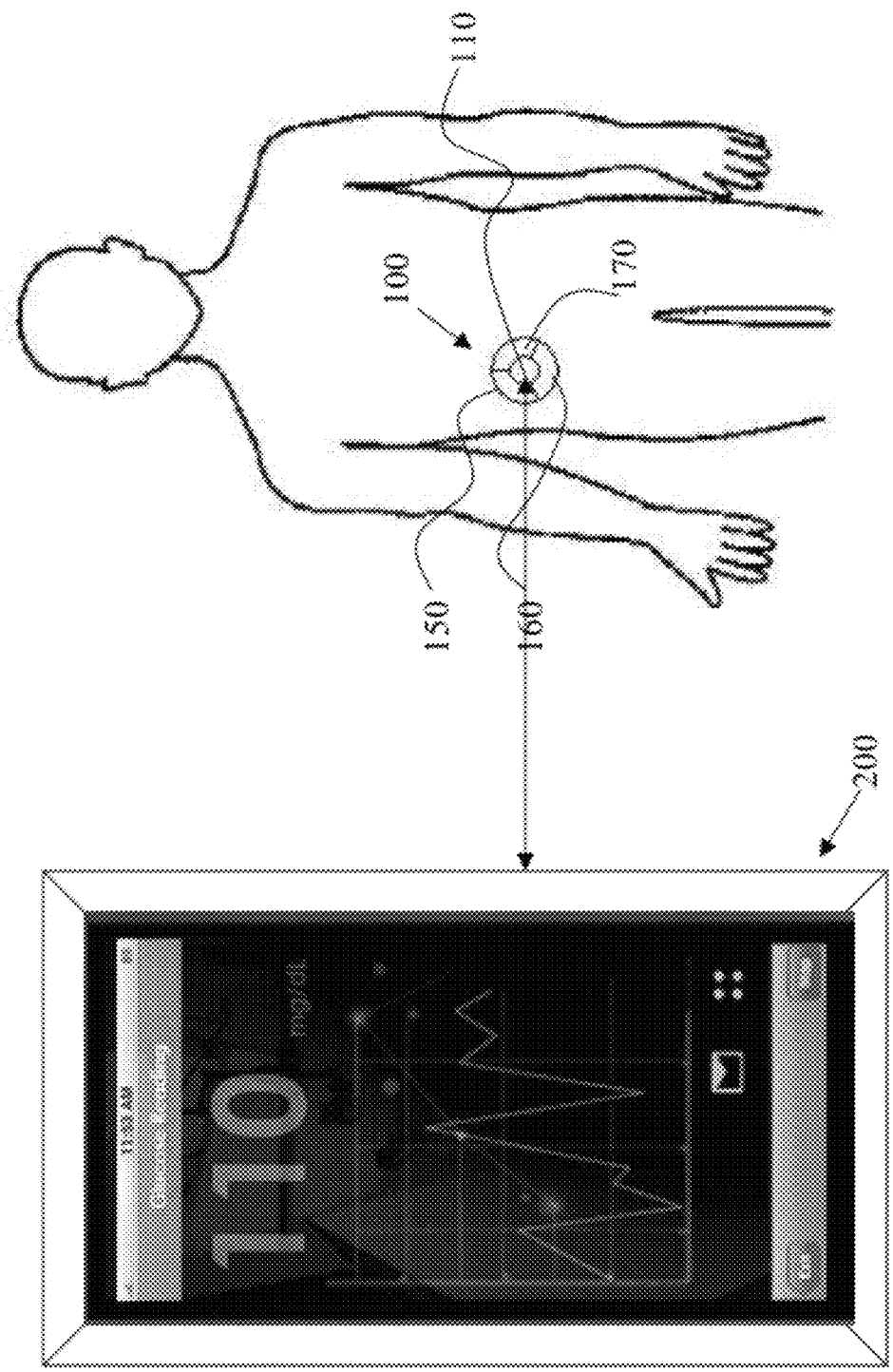
FIG. 7 is a front view of an artificial pancreatic system shown attached to a user and a remote hand-held device for use with the artificial pancreatic system, according to an exemplary embodiment of the present general inventive concept.

FIG. 7 is a front view of an artificial pancreatic system 100 shown attached to a user and a remote hand-held device 200 for use with the artificial pancreatic system 100, according to an exemplary embodiment of the present general inventive concept.

Figure 8:
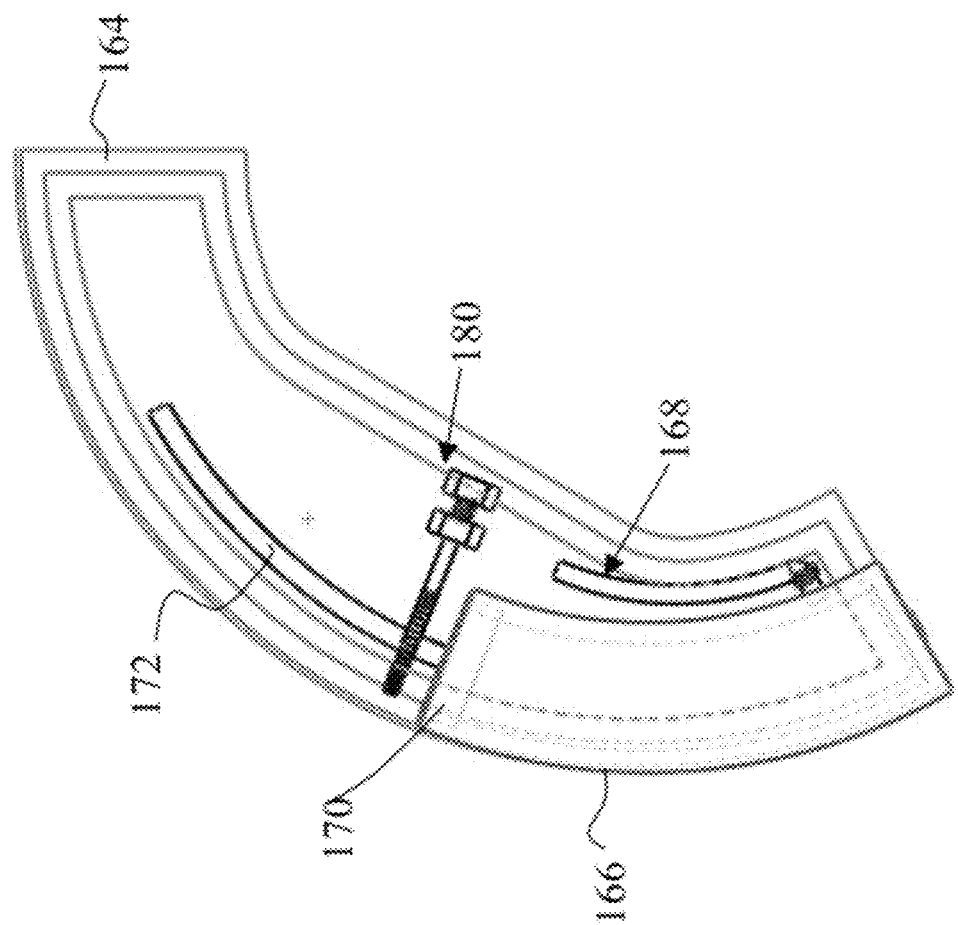
FIG. 8 is a top plan view illustrating a fluid delivery device according to an exemplary embodiment of the present general inventive concept.
Figure 9:
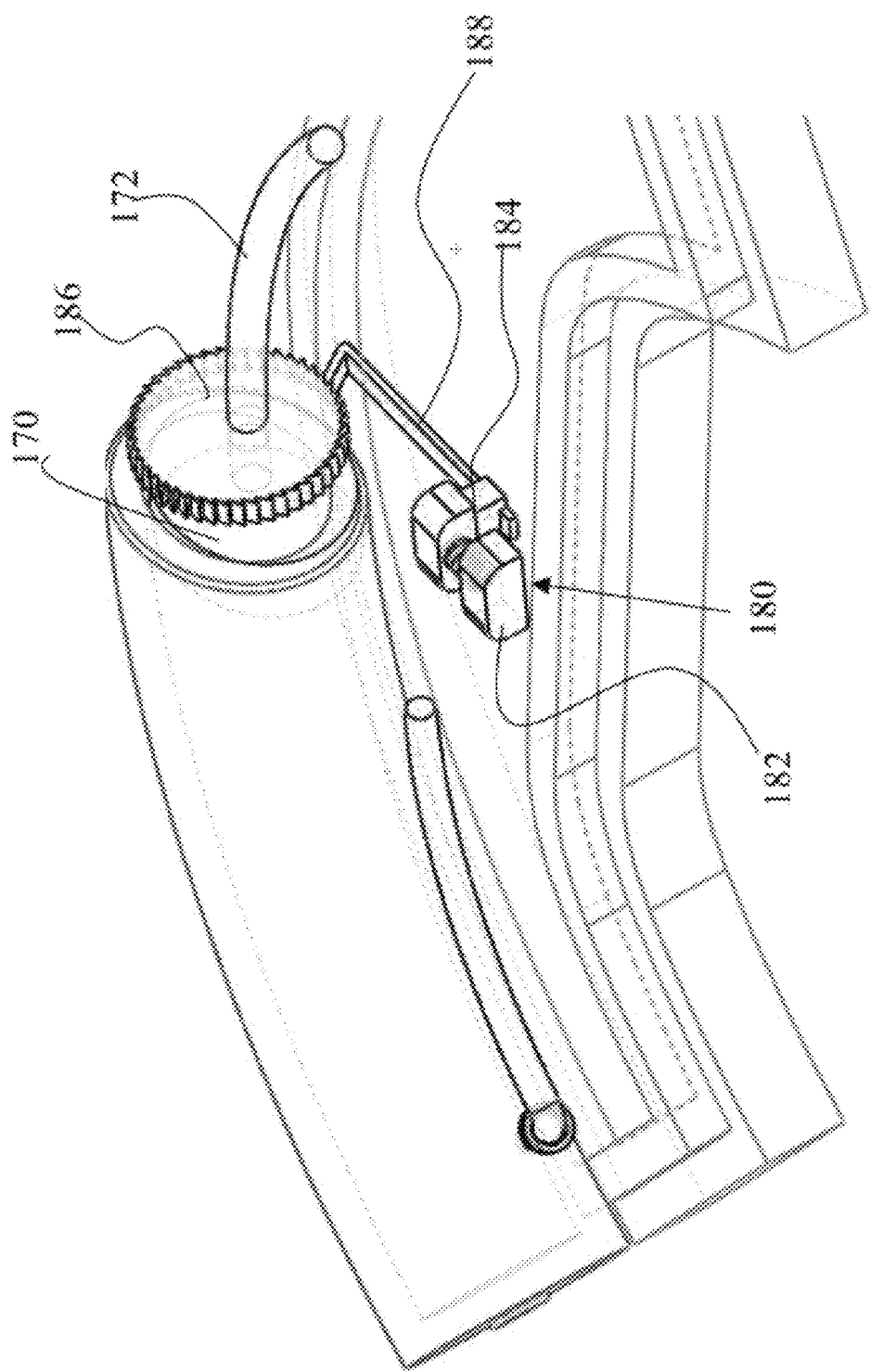
FIG. 9 is a side perspective view illustrating the fluid delivery device of FIG. 8.
Figure 10:
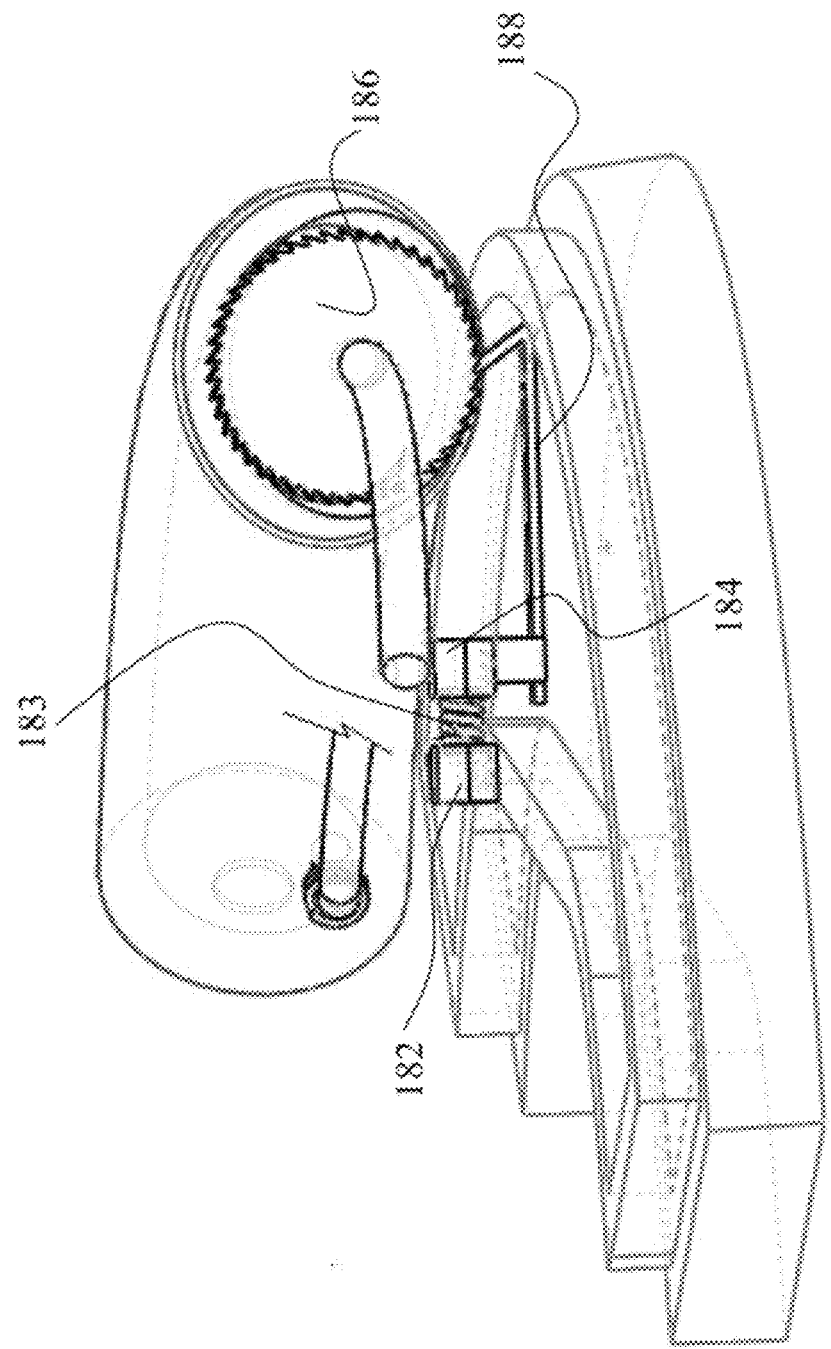
FIG. 10 is a front perspective view illustrating the fluid delivery device of FIG. 8.

FIG. 8 is a top plan view illustrating a fluid delivery device 160, 170 according to an exemplary embodiment of the present general inventive concept, FIG. 9 is a side perspective view illustrating the fluid delivery device 160, 170 of FIG. 8, and FIG. 10 is a front perspective view illustrating the fluid delivery device 160, 170 of FIG. 8.

Referring to FIG. 8, the fluid delivery device 160 includes a fluid delivery wedge base 162 (not illustrated), a fluid delivery wedge cover 164, a fluid storage compartment 166, a needle mechanism 168 having a needle 168A and a flexible cannula 168B to administer the fluid stored in the fluid storage compartment 166 into a user. The needle 168A and cannula 168B are in fluid communication with the fluid storage compartment 166. As illustrated, in an exemplary embodiment, the fluid storage compartment 166 may be formed in an arc shape so as to follow a contour of the fluid delivery wedge cover 164. The fluid delivery device 160 further includes a plunger 170 coupled to a first end of a threaded lead screw 172. The lead screw 172 is formed to follow a center axis of the fluid storage compartment 166. That is, the lead screw 172 may be formed in an arc shape identical to the shape of the fluid storage compartment 166.

Referring to FIG. 9, the fluid delivery device 160 further includes a drive mechanism 180 coupled to a drive wheel 186 through a drive hook 188. The drive wheel 186 is threaded on an interior surface to correspond to the thread of the lead screw 172. That is, as the drive wheel 186 is rotated, the lead screw 172 is driven in a linear motion.

In the current exemplary embodiment, the core apparatus 110 provides a signal to the fluid delivery device 160 to deliver fluid. The drive mechanism 180, which includes an electromagnetic portion 182 and a movable portion 184, is then activated. The movable portion is coupled to the drive hook 188, which is free to travel in a linear direction and is perpendicular to a center axis of the drive wheel 186. As the electromagnetic portion 182 is activated the movable portion 184 is attracted toward the electromagnetic portion 182, thereby creating a rotational force onto the drive wheel 186. When the drive mechanism 180 is activated, the drive wheel 180 is caused to rotate when pulled by the drive hook 188 attached to the movable portion. In addition, a return spring 183 may be disposed between the electromagnetic portion 182 and the movable portion 184 to return the movable portion 184 to an initial position.

In alternative exemplary embodiments, the drive hook 188 may be configured to push against a surface of the drive wheel 186 to cause rotation. While the drive wheel 186 rotates, the lead screw 172 is forced to push the plunger 170 into the fluid storage compartment 166, thereby dispensing the fluid stored therein into the needle mechanism 168 and the user.

Figure 11:
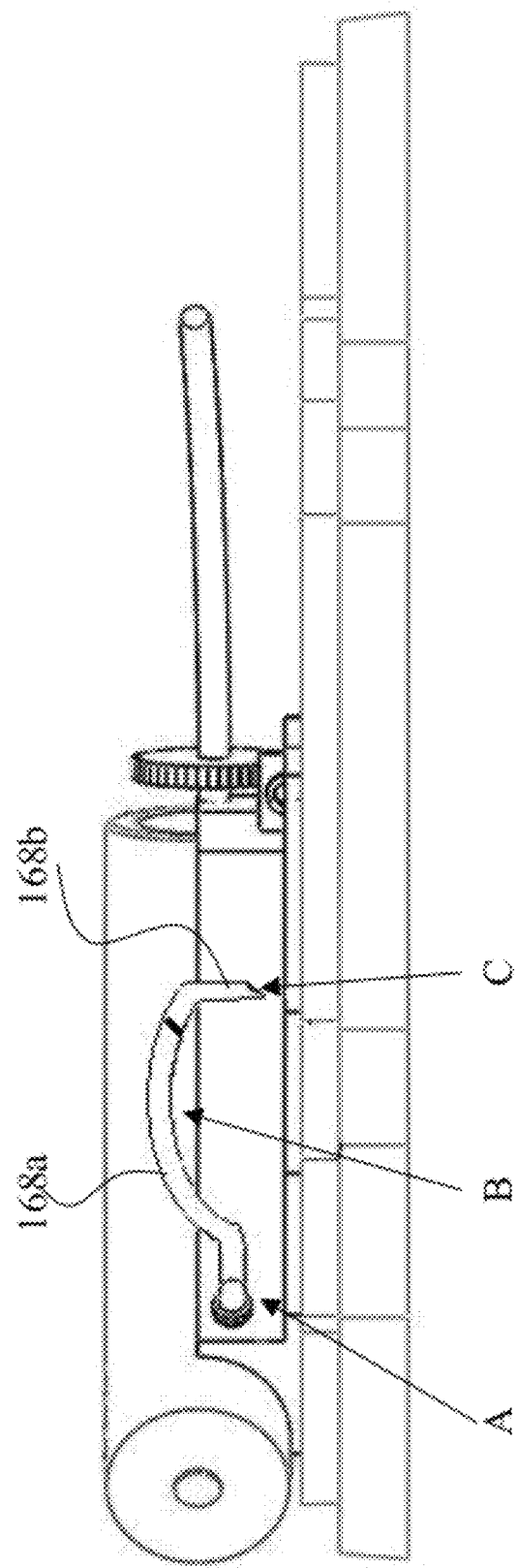
FIG. 11 is a front perspective view illustrating a needle mechanism according to an exemplary embodiment in a bent state.
Figure 12:
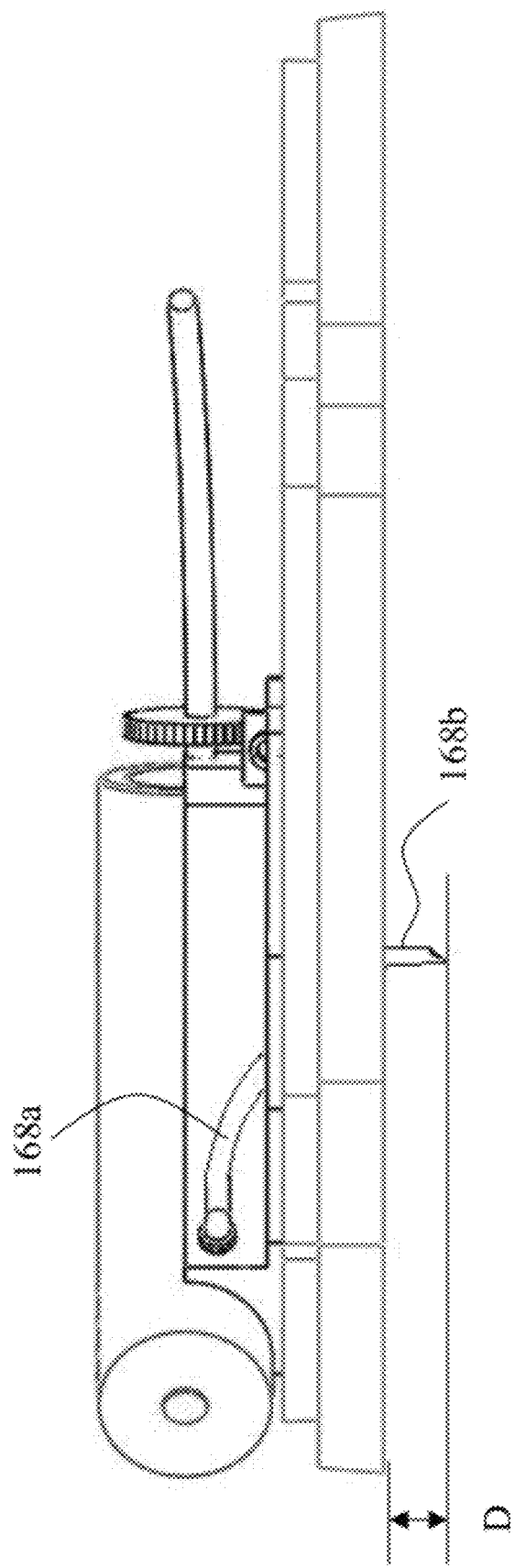
FIG. 12 is a front perspective view illustrating the needle mechanism of FIG. 11 in a deployed state.

FIG. 11 is a front perspective view illustrating a needle mechanism 168 according to an exemplary embodiment in a bent state and FIG. 12 is a front perspective view illustrating the needle mechanism 168 of FIG. 11 in a deployed state.

Referring to FIG. 11, the needle 168A is secured at a first end "A" and bent in a middle portion "B" in an upward direction, such that when released a second end "C" is forced toward the fluid delivery wedge cover 164 and a user. The force of the needle 168A would thereby insert the cannula 168b into the user to a depth "D".

Figure 13:
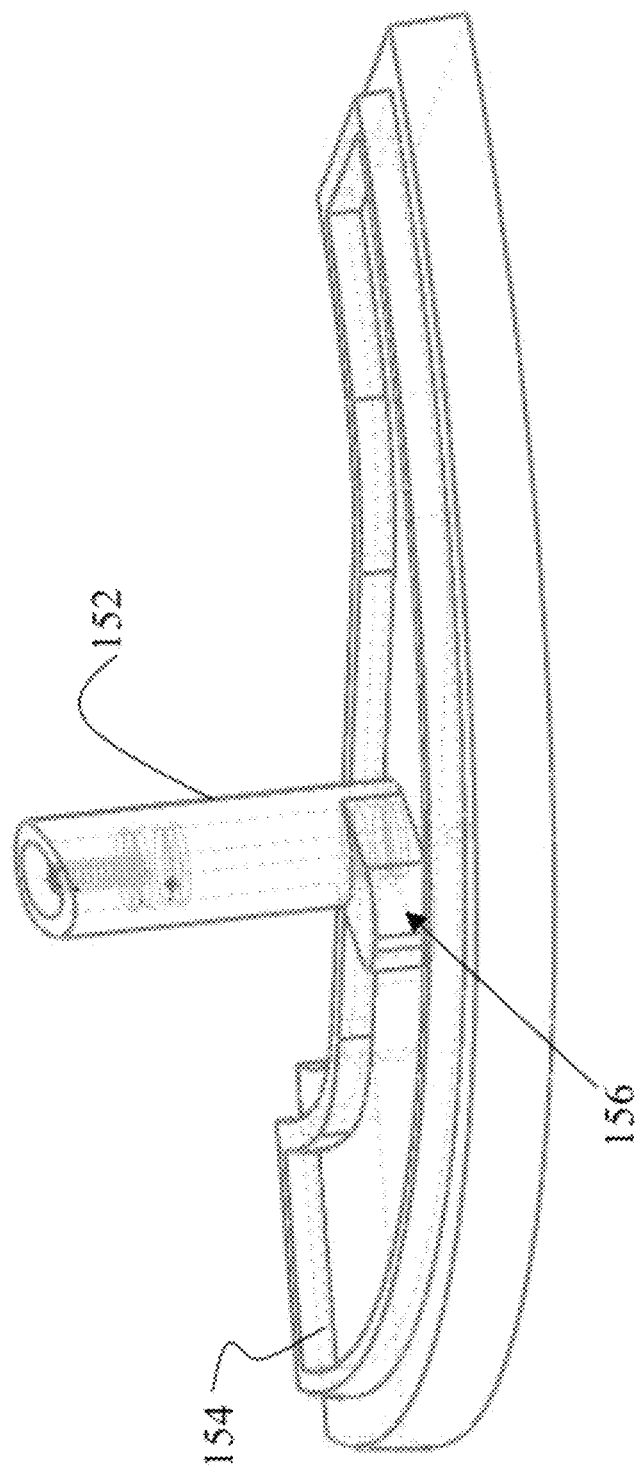
FIG. 13 is a front perspective view illustrating the sensor device according to an exemplary embodiment of the present general inventive concept.
Figure 14A:
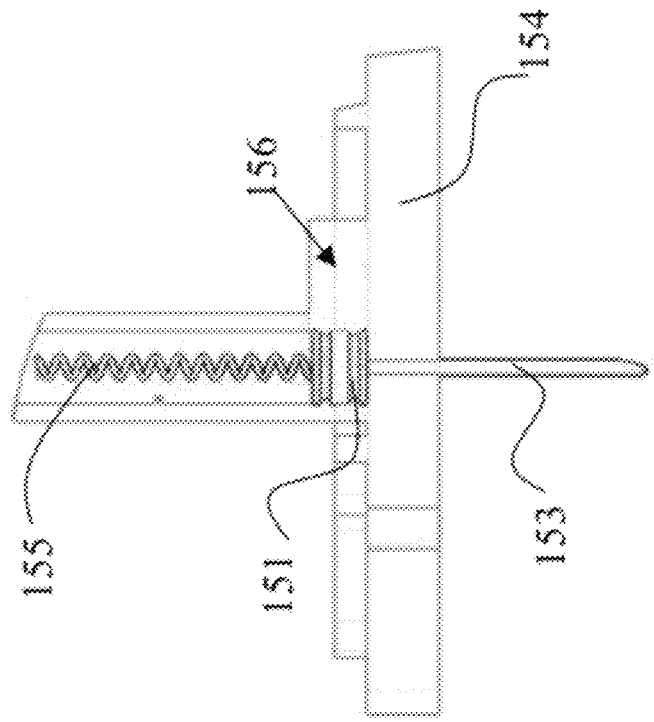
FIG. 14a is a partial cross sectional view of the sensor device of FIG. 13 in a loaded state.

FIG. 13 is a front perspective view illustrating the sensor device 150 according to an exemplary embodiment of the present general inventive concept. FIG. 14a is a partial cross sectional view of the sensor device 150 of FIG. 13 in a loaded state and FIG. 14b is a partial cross sectional view of the sensor device 150 of FIG. 13 in a deployed state.

Referring to FIG. 13, in an exemplary embodiment, the sensor device 150 includes a sensor 151 which is spring loaded within a housing 152 attached to the wedge cover 154. The sensor 151 includes a needle portion 153 which is automatically inserted into a user when instructed to by the external device 200. FIG. 14a illustrates the sensor 151 in a loaded state by compressing a sensor spring 155.

Figure 14B:
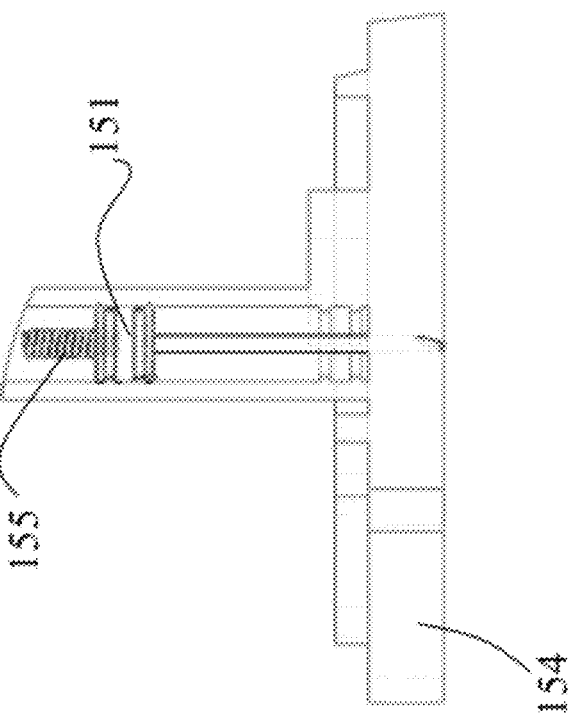
FIG. 14b is a partial cross sectional view of the sensor device of FIG. 13 in a deployed state.

Referring to FIG. 14b, when deployed, the sensor 151 becomes electrically coupled to the sensor device 150 via a electrical hub 156, thereby allowing communication between the sensor 151 and the core apparatus 110. The sensor 151 may measure a user's body signals and transmit this data as a sensor signal to the core apparatus 110.

Figure 15:
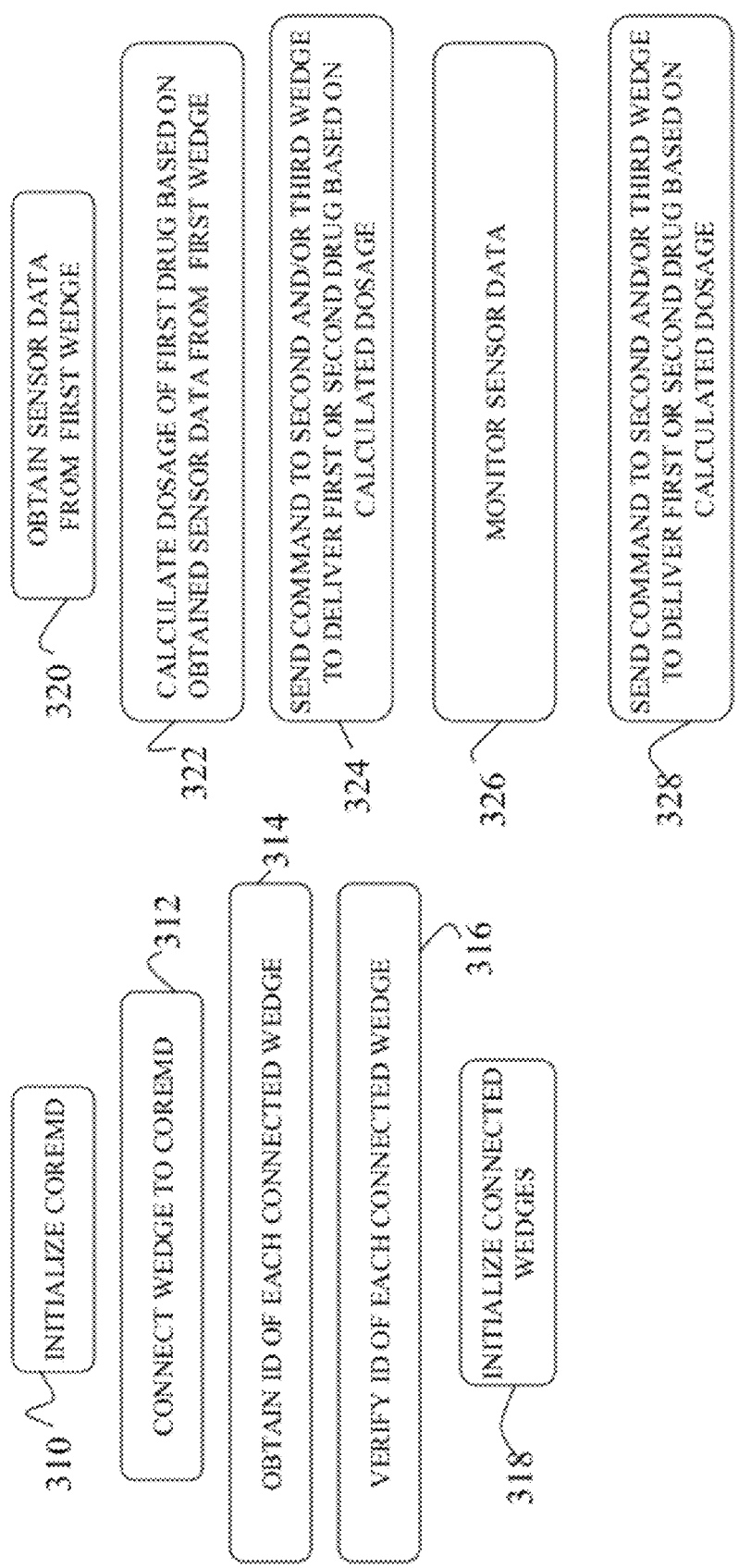
FIG. 15 is a flow chart illustrating a method of using the artificial pancreatic system according to an exemplary embodiment of the present general inventive concept.

FIG. 15 is a flow chart illustrating a method of using the artificial pancreatic system 300 according to an exemplary embodiment of the present general inventive concept. In an exemplary embodiment, the core apparatus 110 (e.g., CoreMD) is initialized 310, a wedge (e.g., a sensor device and/or drug delivery device) is connected to the core apparatus 110 (operation 312). The core apparatus 110 obtains and verifies the identification information from all of the wedges connected to the connection hub 118 of the core apparatus 110, steps 314 and 316. The core apparatus 110 may then initialize each of the connected sensor devices 150 and fluid delivery devices 160, 170. (318)

The identification data of the wedges may then be transmitted to an external device 200 which configures an application on the external device 200 to correspond to the number and types of wedges connected to the connection hub 118.

In operation 320, the sensor 151 is automatically inserted into a user to measure body signals of the user. The sensor 151 will measure and transmit this sensor data to the core apparatus 110. The core apparatus 110 may then transmit the sensor data to the external device 200. The artificial pancreatic system 100 will then calculate dosage information of each fluid or drug disposed within the fluid delivery devices 160, 170 to deliver to the user in order to maintain the user at a predetermined target 322. The appropriate drug delivery devices 160, 170 would receive a deliver command to indicate which type of drug and dosage to deliver to the patient 324. The artificial pancreatic system 100 will automatically and continuously monitor the sensor data received from the sensor devices 150 and instruct the wedges connected to the core apparatus 110 to deliver the appropriate fluids or drugs. (326, 328)

The present general inventive concept also provides users with an affordable, wearable, reusable device which includes low cost disposable sensors and low cost disposable micro infusion pumps. The user wears the device according to the present invention on their body so that his/her body temperature, heart rate, blood pressure, glucose level, etc may be measured by disposable sensors within the sensor device. A smart phone or other wireless device having an application stored thereon monitors the measured body signals and relays the information to the user's healthcare providers via a phone call, text message, email, website, or other wireless communication.

In alternative embodiments, the device may also perform remote subcutaneous fluid delivery of medication to the user. That is, under a secured communication protocol, the healthcare provider may instruct the device to remotely administer a medication stored within the fluid device to the user. This would substantially reduce the amount of re-hospitalization of patients during the critical days after a patient is discharged from a healthcare facility.

Although a few exemplary embodiments of the present general inventive concept have been illustrated and described, it will be appreciated by those skilled in the art that changes may be made in these exemplary embodiments without departing from the principles and spirit of the general inventive concept, the scope of which is defined in the appended claims and their equivalents.

What is claimed is:

1. A core apparatus connectable to at least one sensor and to at least one fluid delivery device, the core apparatus comprising:
    a base housing;
    a connection hub to couple to the at least one sensor and to the at least one fluid delivery device;
    a controller disposed within the base housing to communicate with and control the at least one sensor and the at least one fluid delivery device; and
    a power source having an induction circuit to inductively power at least one of the at least one sensor and the at least one fluid delivery device,
    wherein the controller calculates an amount of fluid to be delivered from the fluid delivery device and forms a continuous feedback loop with the at least one sensor and the at least one fluid delivery device.

2. The core apparatus of claim 1, wherein the controller controls operations of the at least one sensor and the at least one fluid delivery device.

3. The core apparatus of claim 1, wherein the at least one sensor is connectable to a user to measure the user's body signals.

4. The core apparatus of claim 3, wherein the body signals include the user's blood glucose level, vital readings, cholesterol, analytes, hormone, blood pressure, and Oxygen level.

5. The core apparatus of claim 1, wherein the at least one sensor and the at least one fluid delivery device are formed to surround the base housing.

6. The core apparatus of claim 5, wherein the base housing is formed in a triangular shape, a rectangular shape, a circular shape, a pentagon shape, or a combination thereof.

7. The core apparatus of claim 1, wherein the fluid delivery device delivers a fluid stored therein to a user.

8. The core apparatus of claim 7, wherein the fluid includes at least one of insulin and glucagon.

9. The core apparatus of claim 1, wherein the controller controls operations of each of the at least one sensor and the at least one fluid delivery device attached to the connection hub.

10. The core apparatus of claim 1, further comprising a power source disposed within the base housing to provide voltage to the controller, to the at least one sensor, and to the at least one fluid delivery device.

11. The core apparatus of claim 1, wherein the controller wirelessly communicates to an external device to control an operation of the at least one sensor and the at least one fluid delivery device.

12. A health treatment system, comprising:
    a core apparatus having a CPU in communication with an external device and a power source having an induction circuit, the external device having a plurality of configurations;
    a sensor device having a sensor to detect a body signal from a user connectable to the core apparatus; and
    a first fluid delivery device having a first fluid storage compartment to store a first fluid and a first fluid dispensing mechanism to deliver the first fluid to the user connectable to the core apparatus;
    wherein the core apparatus instructs the external device to operate in a first configuration when only the at least one sensor device is coupled to the core apparatus, a second configuration when only the first fluid delivery device is coupled to the core apparatus, and a third configuration when both the at least one sensor device and the first fluid delivery device are coupled to the core apparatus, and
    wherein the CPU of the core apparatus calculates an amount of the first fluid to be delivered from the first fluid delivery device and an amount of the second fluid to be delivered from the second fluid delivery device, and
    wherein the induction circuit inductively powers at least one of the sensor device and the first fluid delivery device.

13. The health treatment system of claim 12, further comprising a second fluid delivery device having a second fluid storage compartment to store a second fluid and a second fluid dispensing mechanism to deliver the second fluid to the user.

14. The health treatment system of claim 13, wherein the external device is a mobile device.

15. The health treatment system of claim 14, wherein the core apparatus communicates to the external device through at least one of Bluetooth™, Bluetooth Low Energy™, WiFi, Zigbee™, ANT™, and ANT+™.

16. The health treatment system of claim 13, wherein the sensor of the at least one sensor device includes a glucose sensor, a cholesterol sensor, a blood pressure sensor, an oxygen sensor, an analyte sensor, a heart rate sensor, and a body temperature sensor.

17. The health treatment system of claim 13, wherein the core apparatus transmits and receives data to/from the external device to allow for a continuous feedback loop between the at least one sensor device, the first fluid delivery device, the second fluid delivery device, and the external device.

18. The health treatment system of claim 13, wherein the at least one sensor is attached to a user to measure the user's glucose level and to transmit a sensor data corresponding to the measured glucose level to the core apparatus, the core apparatus to control the first fluid delivery device and the second fluid delivery device to deliver the first and second fluid according to the user's predetermined limits.

19. The health treatment system of claim 18, wherein the user's predetermined limits are stored within the external device.

20. The health treatment system of claim 12, wherein the core apparatus instructs the external device to operate in a fourth configuration when the at least one sensor device, the first fluid delivery device, and the second fluid delivery device are coupled to the core apparatus.

21. A method of using a disease management system, the method comprising:
    removably attaching a sensor device to a core apparatus, the core apparatus having a power source having an induction circuit, a sensor to measure a body signal of a user and a controller to control an operation of the core apparatus;
    removably attaching a first fluid delivery system to the core apparatus, the first fluid delivery system having a first fluid compartment and a first fluid delivery device to store and deliver a first fluid; and removably attaching a second fluid delivery system to the core apparatus, the second fluid delivery system having a second fluid compartment and a second fluid delivery device to store and deliver a second fluid, wherein the core controller receives the body signal from the sensor device, calculates an amount of the first and second fluid to be delivered, and controls the delivery of the first fluid and the second fluid based on the body signal, and wherein the induction circuit inductively powers at least one of the sensor device, the first fluid delivery device, and the second fluid delivery device.

\* \* \* \* \*